US012788895B2

(12) United States Patent
Wilson et al.

(10) Patent No.: US 12,788,895 B2
(45) Date of Patent: Nov. 10, 2026

(54) INJECTOR DEVICE

(71) Applicant: SANOFI-AVENTIS DEUTSCHLAND GMBH, Frankfurt am Main (DE)

(72) Inventors: Robbie Wilson, Melbourn (DE); Harpal Singh, Melbourn (DE); Matthew Young, Melbourn (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 71 days.

(21) Appl. No.: 16/347,726

(22) PCT Filed: Oct. 12, 2017

(86) PCT No.: PCT/EP2017/076108
§ 371 (c)(1),
(2) Date: May 6, 2019

(87) PCT Pub. No.: WO2018/086817
PCT Pub. Date: May 17, 2018

(65) Prior Publication Data
US 2019/0282761 A1 Sep. 19, 2019

(30) Foreign Application Priority Data
Nov. 9, 2016 (EP) .................................... 16197955

(51) Int. Cl.
*A61M 5/315* (2006.01)
*A61M 5/20* (2006.01)

(52) U.S. Cl.
CPC ........ *A61M 5/3157* (2013.01); *A61M 5/2033* (2013.01); *A61M 5/31501* (2013.01);
(Continued)

(58) Field of Classification Search
CPC ........... A61M 5/3157; A61M 5/31568; A61M 5/1684; A61M 5/31583; A61M 2005/208;
(Continued)

(56) References Cited

U.S. PATENT DOCUMENTS 6,585,698 B1 7/2003 Packman et al.
2003/0105430 A1 6/2003 Lavi et al.
(Continued)

FOREIGN PATENT DOCUMENTS

CN 102648014 8/2012
CN 104582762 4/2015
(Continued)

OTHER PUBLICATIONS

International Search Report and Written Opinion in Application No. PCT/EP2017/076108, dated Jan. 9, 2018, 12 pages.
(Continued)

*Primary Examiner* — Kami A Bosworth
*Assistant Examiner* — Avery Smale
(74) *Attorney, Agent, or Firm* — Fish & Richardson P.C.

(57) ABSTRACT

The present disclosure relates to an injector device having a container and a plunger. The plunger is movable into the container to dispense medicament during operation of the injector device. The injector device also has a switch arranged to interact with a structural element of the plunger to detect movement of the plunger during operation of the injector device.

17 Claims, 12 Drawing Sheets

(52) U.S. Cl.
CPC .... *A61M 5/31511* (2013.01); *A61M 5/31568* (2013.01); *A61M 5/31578* (2013.01); *A61M 2005/2073* (2013.01); *A61M 2005/31508* (2013.01); *A61M 2207/00* (2013.01)

(58) Field of Classification Search
CPC ...... A61M 2005/2073; A61M 5/31501; A61M 5/31585; A61M 5/3202; A61M 2005/31508; A61M 2205/3327; A61M 2205/3569; A61M 2205/50; A61M 2005/2013; A61M 2205/583; A61M 2207/00; A61M 5/20; A61M 2005/2026; A61M 5/2033; A61M 5/31511; A61M 5/31571; A61M 2005/31588; A61M 2205/82; A61M 2205/8206; A61M 2205/8212
See application file for complete search history.

(56) References Cited

U.S. PATENT DOCUMENTS

| | | | | |
|---|---|---|---|---|
| 2009/0209939 | A1 | 8/2009 | Verespej et al. | |
| 2014/0148763 | A1* | 5/2014 | Karlsson | A61M 5/31583 604/221 |
| 2014/0296787 | A1* | 10/2014 | Agard | A61M 5/172 604/152 |
| 2016/0259913 | A1* | 9/2016 | Yu | A61M 5/31511 |
| 2017/0007765 | A1* | 1/2017 | Cowe | A61M 5/24 |
| 2017/0354779 | A1* | 12/2017 | Atterbury | A61M 5/3157 |
| 2019/0111211 | A1* | 4/2019 | Verhoeven | A61M 5/31505 |

FOREIGN PATENT DOCUMENTS

| | | | | |
|---|---|---|---|---|
| CN | 106029127 | | 10/2016 | |
| EP | 1240913 | | 9/2002 | |
| EP | 2510961 | | 10/2012 | |
| EP | 2756855 | | 7/2014 | |
| JP | 2001-170176 | | 6/2001 | |
| JP | 2002-272839 | | 9/2002 | |
| JP | 2014-519922 | | 8/2014 | |
| JP | 2017-536177 | | 12/2017 | |
| TW | 201210647 | | 3/2012 | |
| WO | WO 03/082381 | | 10/2003 | |
| WO | WO-2012122643 | A1 * | 9/2012 | A61M 5/2033 |
| WO | WO-2012160159 | A1 * | 11/2012 | A61M 5/20 |
| WO | WO 2012/173553 | | 12/2012 | |
| WO | WO 2013/113818 | | 8/2013 | |
| WO | WO 2015/118358 | | 8/2015 | |
| WO | WO-2015144870 | A1 * | 10/2015 | A61M 5/2033 |
| WO | WO 2016/038498 | | 3/2016 | |
| WO | WO 2016/078863 | | 5/2016 | |
| WO | WO-2017097507 | A1 * | 6/2017 | A61M 5/2033 |
| WO | WO-2017129314 | A1 * | 8/2017 | G16H 20/17 |

OTHER PUBLICATIONS

International Preliminary Report on Patentability in Application No. PCT/EP2017/076108, dated May 14, 2019, 9 pages.

* cited by examiner

INJECTOR DEVICE

CROSS REFERENCE TO RELATED APPLICATIONS

The present application is the national stage entry of International Patent Application No. PCT/EP2017/076108, filed on Oct. 12, 2017, and claims priority to Application No. EP 16197955.4, filed on Nov. 9, 2016, the disclosures of which are incorporated herein by reference.

TECHNICAL FIELD DISCLOSURE

The present disclosure relates to an injector device for a medicament.

BACKGROUND

Injector devices, such as auto-injectors, typically have a syringe into which a plunger is pushed to dispense medicament from the syringe. The amount of medicament in the syringe is pre-determined and the plunger must complete its movement into the syringe such that the appropriate amount of medicament in the syringe is dispensed.

SUMMARY

It is an object of the present disclosure to provide an advantageous injector device having a container and a plunger that is movable within the container to dispense medicament during operation of the injector device.

According to the present disclosure, there is provided an injector device comprising:

- a container and a plunger that is movable into the container to dispense medicament during operation of the injector device; and,
- a switch arranged to interact with a structural element of the plunger to detect movement of the plunger during operation of the injector device.

The plunger may be configured to move from a first position to a second position to dispense medicament from the container. The switch may be arranged to interact with the structural element of the plunger at the first position and/or the second position.

The switch may be arranged to detect the start of the movement of the plunger and/or the end of the movement of the plunger. Alternatively or additionally, the switch may be arranged to detect the plunger at a point along its movement into the container.

The structural element of the plunger may be a recess or a protrusion. Alternatively or additionally, the structural element of the plunger may be an end of the plunger.

Examples of the injector device may comprise a first switch arranged to detect a recess or protrusion of the plunger, and a second switch arranged to detect an end of the plunger as the plunger moves into the container. The injector device may further comprise a housing having a distal end and a proximal end, the first switch being mounted distally of the second switch within the housing. In this example, the distal end is relatively closer to the site of injection than the proximal end.

The injector device may further comprise a biasing member arranged to push the plunger into the container during operation of the device, and a latch arranged to hold the plunger in an initial position where the biasing member is under compression prior to operation of the injector device.

The plunger may be configured to be rotated to disengage the latch. In this example, the switch may be arranged to be aligned with the structural element of the plunger after the plunger has been rotated. Alternatively or additionally, the switch may be arranged to detect the structural element of the plunger when the plunger is rotated to disengage the latch.

The latch may comprise a collar that surrounds a part of the plunger and engages the plunger to hold the plunger in the initial position. In this example, the plunger may be arranged to be rotated relative to the collar to release the plunger for movement into the container.

The injector device may further comprise a needle sleeve slidably mounted in the injector device and arranged such that during use the needle sleeve slides into engagement with the plunger to cause the plunger to rotate and disengage the latch.

In other embodiments, the injector device includes a collar that surrounds a part of the plunger. The collar engages the plunger and holds the plunger in the initial position, with the biasing member under compression prior to operation of the device. The collar can be rotated, for example manually or by an actuator, to release the plunger for movement into the container.

The switch may comprise a mechanical switch having an engaging member that contacts the plunger. The engaging member may be spring-loaded such that the engaging member is pushed against a surface of the plunger. In this way, the engaging member will engage with a structural element of the plunger as the structural element passes the engaging member.

The injector device may further comprise a communication device configured to receive a signal output by the switch.

The communication device may comprise an antenna. The antenna may be integrally formed in a part of a housing of the injector device. Alternatively, the antenna may be located inside a housing of the injector device. Alternatively, the antenna may be provided in an adhesive label that is attached to an outer surface of the injector device. In some examples, the antenna may be connected to further electronic components of the injector device via electrical connections formed that extend through a housing of the injector device.

The communication device may be configured to communicate with an external device. The communication device may be a transmitter, for example a radio transmitter. In another example, the communication device comprises a BLUETOOTH® device. In another example, the communication device comprises a near-field communication (NFC) chip or device.

The further device may for example be an auxiliary device for communicating with the injector device. In this example, the auxiliary device may connect with more than one injector device. In other examples, the further device may be a smartphone or other handheld electronic device. The auxiliary device or the handheld electronic device may have software, for example an application (app), for connecting with, and receiving information from, the injector device.

The injector device may further comprise a processing unit configured to receive a signal output by the switch. The processing unit may process the signal, for example to determine movement of the plunger. The processing unit may be in communication with the communication unit, if provided, and may provide a signal to the communication unit.

The injector device may further comprise a feedback device configured to provide a user with information relating to movement of the plunger during operation of the injector device. The feedback device may comprise a screen, or other visual display, such as one or more LED's.

The injector device may further comprise a reservoir of liquid medicament.

According to a further aspect of the present disclosure there is provided a method of operating an injector device, the injector device comprising a container and a plunger, the method comprising:

- moving the plunger into the container to dispense medicament; and,
- detecting a structural element of the plunger as the plunger moves into the container, to detect movement of the plunger.

The method may further comprise the steps of rotating the plunger to release the plunger from a latched position so that the plunger moves into the container, and detecting the structural element of the plunger after the plunger has been rotated.

According to a further aspect of the disclosure, there is provided a method of manufacturing an injector device, comprising arranging a container and a plunger such that the plunger is moveable into the container to dispense medicament during operation of the injector device; and, providing a switch arranged to interact with a structural element of the plunger to detect movement of the plunger during operation of the injector device.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying drawings, in which:

FIG. 9C is a perspective view of an alternative plunger for the injector device of any of FIG. 2A to FIG. 8C;

DETAILED DESCRIPTION

Figure 1A:
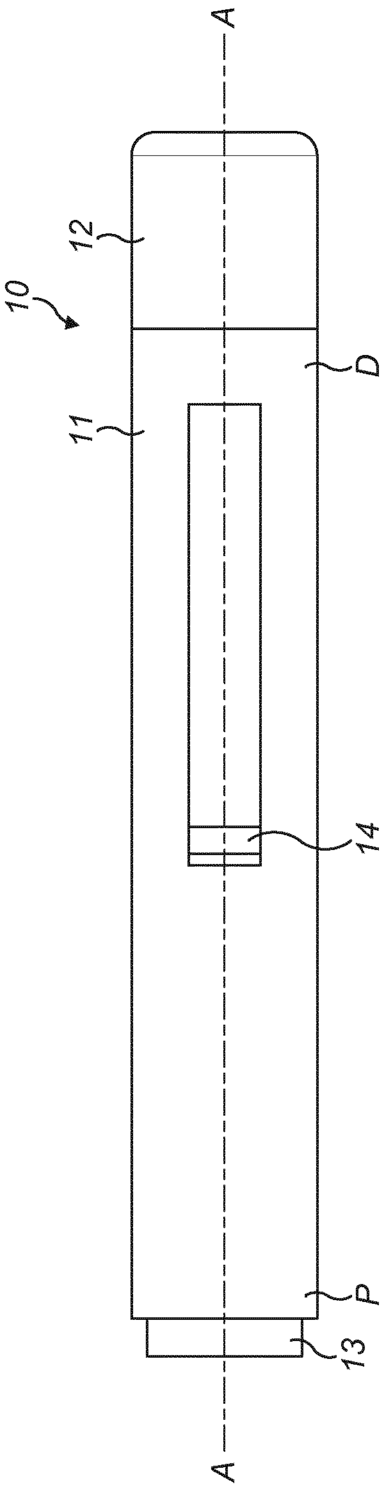
FIG. 1A is a schematic side view of an injector device and a removable cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
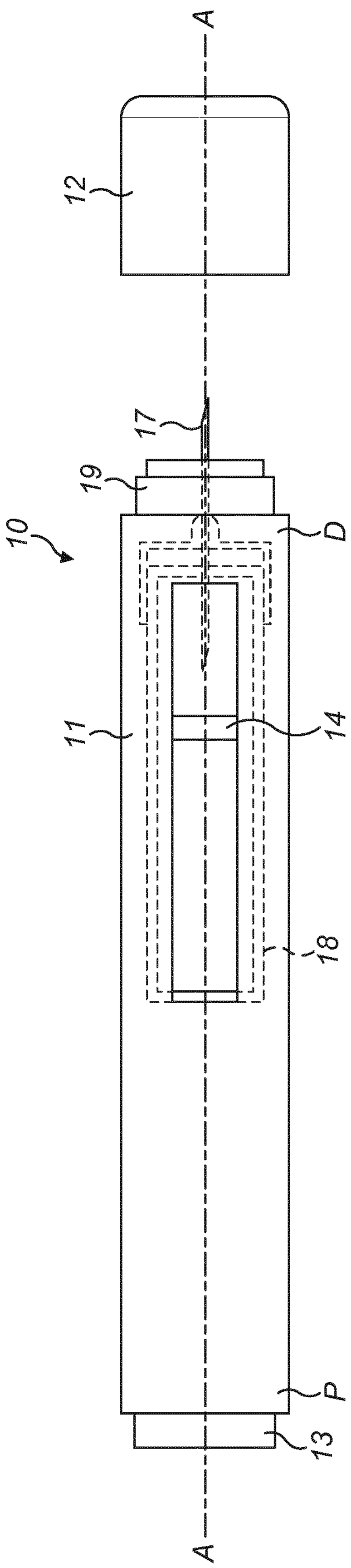
FIG. 1B is a schematic side view of the injector device of FIG. 1A, with the cap removed from the housing.

According to some embodiments of the present disclosure, an exemplary drug delivery device is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2A:
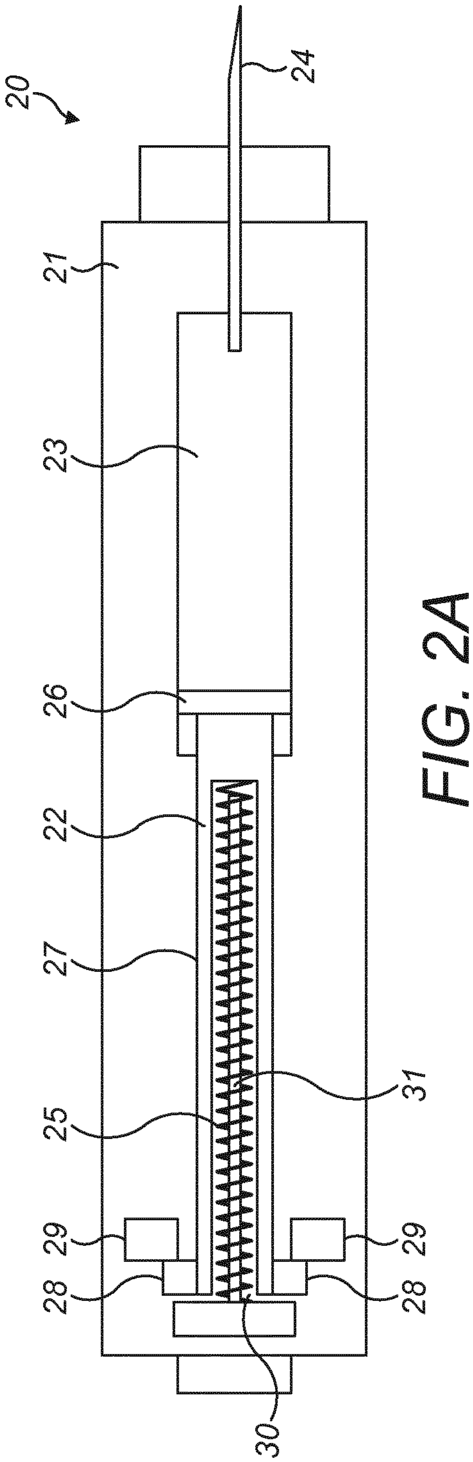
FIG. 2A is a schematic side view of an injector device having a spring to push a plunger into a syringe, the injector device is in a pre-dose position.
Figure 2B:
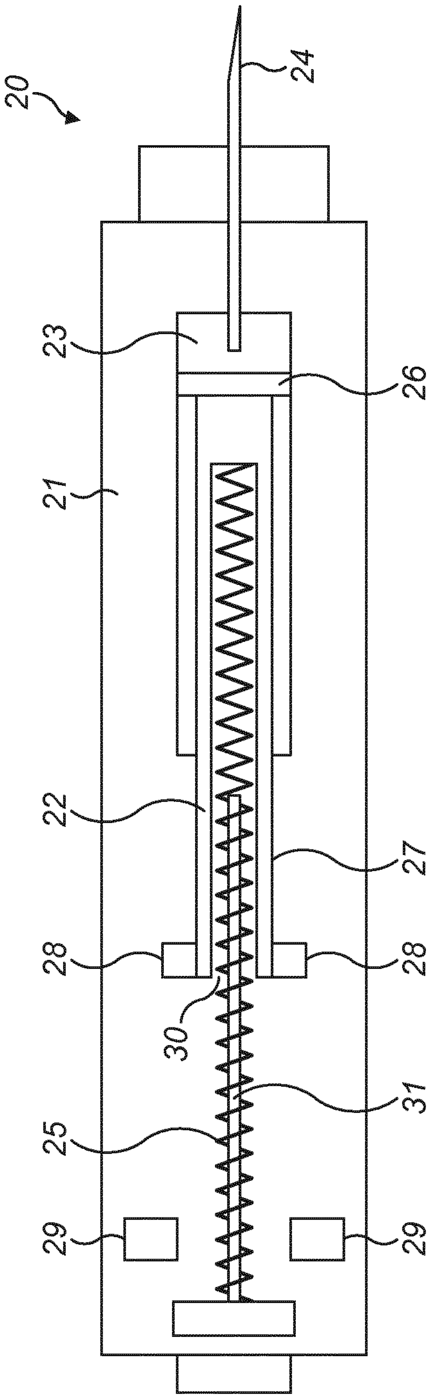
FIG. 2B is a schematic side view of the injector device of FIG. 2A, in a post-dose position.

FIG. 2A and FIG. 2B show an example injector device 20 comprising a housing 21, a plunger 22 and a syringe 23 similar to the example of FIG. 1A and FIG. 1B. The injector device 20 also comprises a needle 24 through which medicament is dispensed when the plunger 22 is pushed into the syringe 23. In this example, the injector device 20 includes a spring 25 arranged to push the plunger 22 into the syringe 23 to force medicament through the needle 24 during use of the injector device 20.

As shown in FIG. 2A, a piston 26 is located in the syringe 23 and a plunger rod 27 acts on the piston 26 to push the piston 26 through the syringe 23 and thereby dispense medicament through the needle 24. The plunger rod 27 and piston 26 may be separate components or a single component, and together they form the plunger 22.

As illustrated, the plunger 22 has locking tabs 28 that engage with parts 29 of the housing 21 in the position shown in FIG. 2A to form a latch. In the latched position, shown in FIG. 2A, the spring 25 is compressed and urges the locking tabs 28 on the plunger 22 against the parts 29 of the housing 21 such that plunger 22 is held in position.

The latch may be released by disengaging the locking tabs 28 from the parts 29 of the housing 21. The latch may be disengaged, for example, by rotating the plunger 22 relative to the housing 21. In another example, the latch may be disengaged by retracting the parts 29 of the housing 21. Rotation of the plunger 22 or retraction of the parts 29 may be actuated by moving a part of the injector device 20, or by a button or latch, as previously described.

In one example, the latch is disengaged by rotating the plunger 22, and the plunger 22 is caused to rotate by an actuator. The actuator extends from the housing 21 proximal to the needle 24 and is pushed against the skin of a user during use of the device 20. When pushed against the skin the actuator is moved within the housing 21 and causes rotation of the plunger 22.

As shown in FIG. 2A and FIG. 2B, the plunger 22 has an opening 30 at the proximal end into which the spring 25 extends. The housing 21 includes a spigot 31 that extends through the spring 25 and into the opening of the plunger 22 when in the position shown in FIG. 2A. The opening 30 and spigot 31 help to stabilise the position of the spring 25 and prevent the spring 25 from becoming misaligned within the injector device 20, which may result in the spring 25 not being positioned correctly to push the plunger 22 into the syringe 23.

FIG. 2B shows the injector device 20 after the latch has been released and the spring 25 has pushed the plunger 22 into the syringe 23 and forced medicament out of the needle 24.

Accordingly, FIG. 2A shows the plunger 22 in a first position, otherwise called a pre-dose position. FIG. 2B shows the plunger 22 in a second position, otherwise called a post-dose position.

Figure 3A:
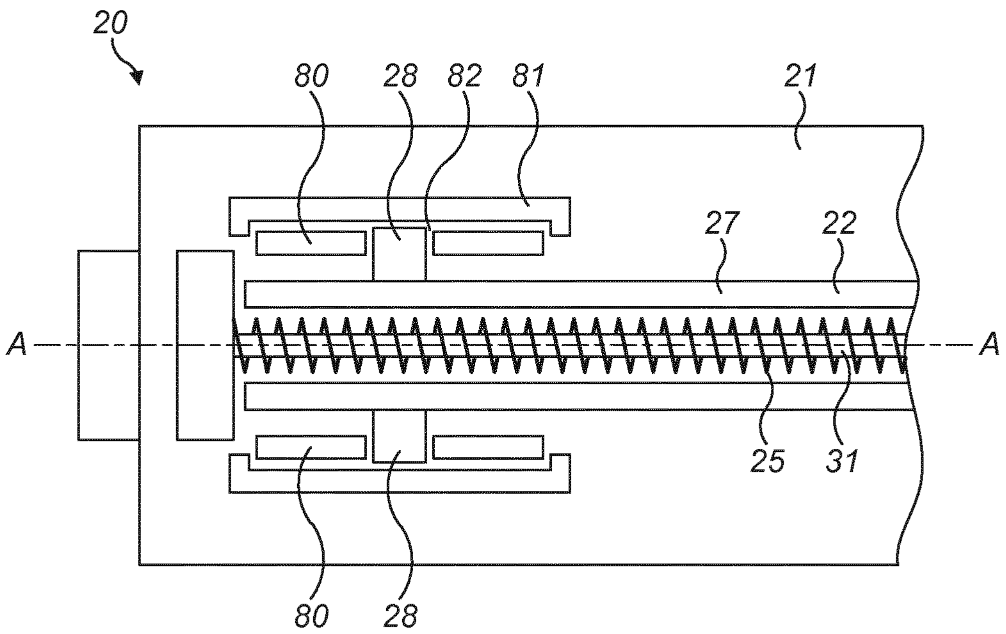
FIG. 3A is a schematic side view of a part of an injector device having an alternative latch, in a pre-dose position.
Figure 3B:
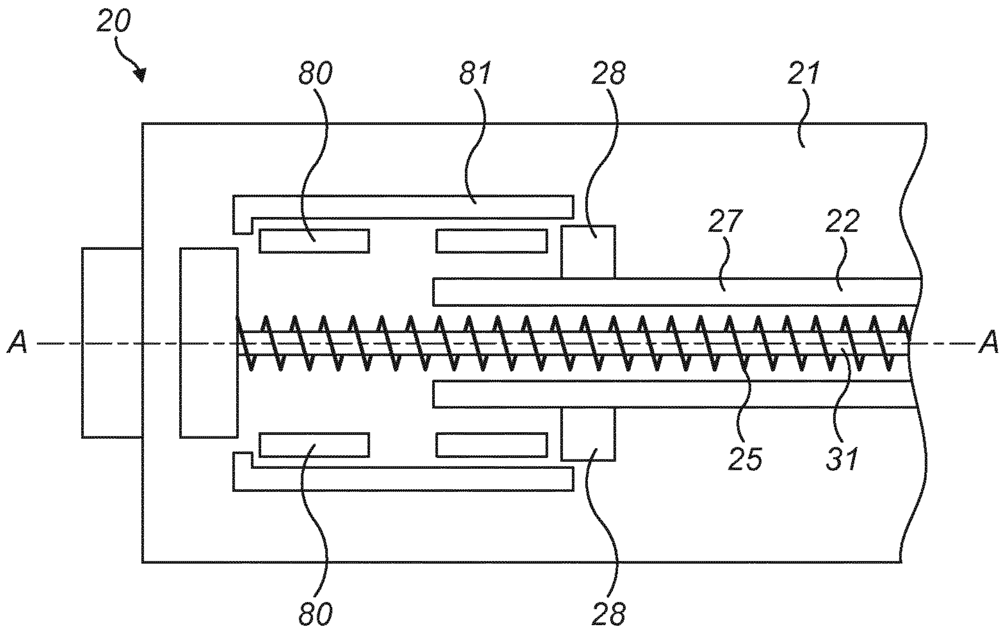
FIG. 3B is a schematic side view of the injector device of FIG. 3A, in a post-dose position.

In another example, schematically illustrated in FIG. 3A and FIG. 3B, a collar 80 is provided that surrounds a proximal part of the plunger 22. The collar 80 is shown in cross-section in FIG. 3A and FIG. 3B. The collar 80 is retained in position relative to the housing 21 by retaining member 81, but the collar 80 is able to rotate about the longitudinal axis A-A. The collar 80 includes a slot 82 that holds the locking tabs 28 of the plunger 22 until the collar 80 is rotated into a release position, as described below.

Figure 3C:
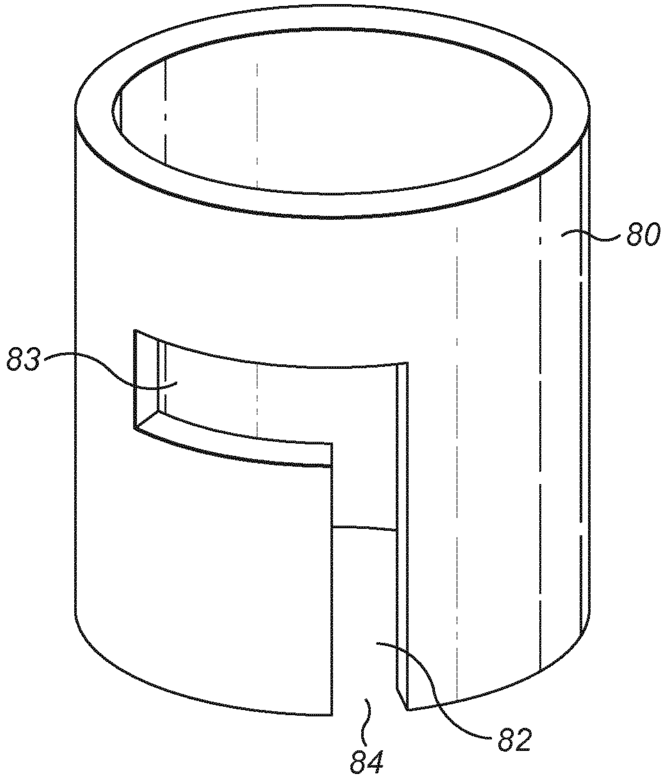
FIG. 3C is a perspective view of a collar of the injector device of FIG. 3A.

As shown in FIG. 3C, the slot 82 is 'L-shaped', and there is one slot 82 for each locking tab 28. In this way, rotation of the collar 80 moves the locking tab 28 from the retaining part 83 of the slot 82 to the release part 84 of the slot. In the release part 84 the plunger 22 can be pushed into the syringe by the spring 25, as shown in FIG. 3B.

Figure 4A:
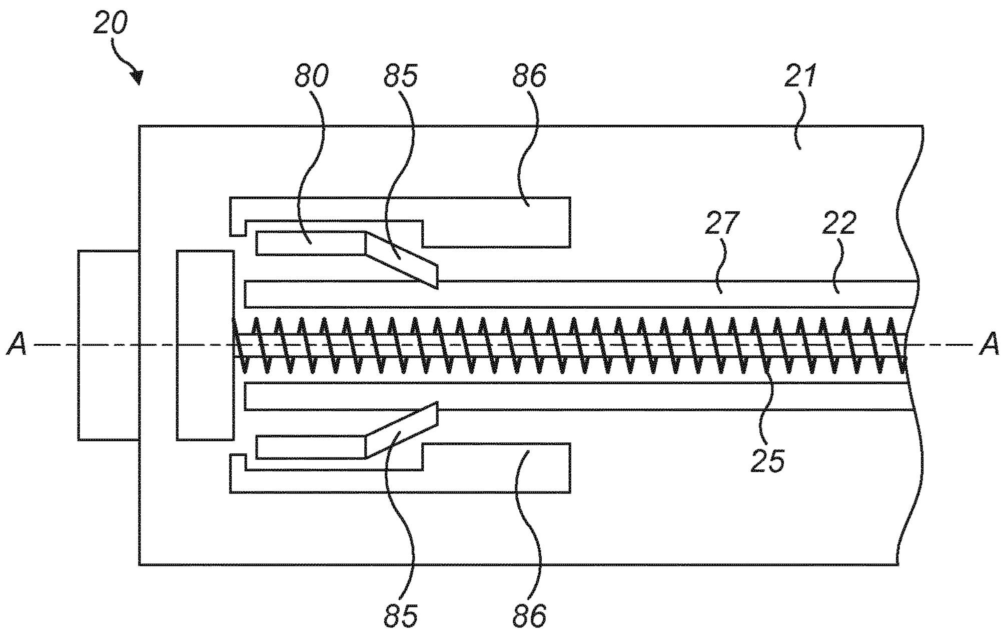
FIG. 4A is a schematic side view of a part of an injector device having an alternative latch, in a pre-dose position.
Figure 4B:
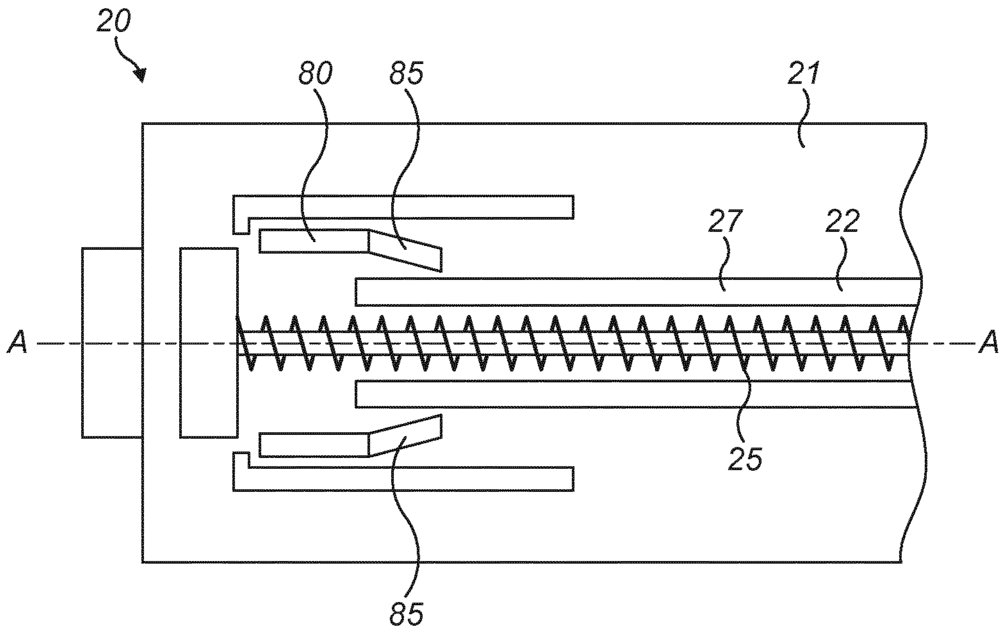
FIG. 4B is a schematic side view of the injector device of FIG. 4A, in a post-dose position.

In an alternative embodiment, illustrated in FIG. 4A and FIG. 4B, the collar 80 includes engaging arms 85 that hold the plunger 22 in the initial position until the collar 80 is rotated. In this example, before rotation a locking portion 86 of the housing 21 may be arranged to hold the engaging arms 85 in a position that holds the plunger 22 in the spring-loaded position. The engaging arms 85 are held in engagement with the plunger 22 and in this position do not permit movement of the plunger 22. Rotation of the collar 80 about the longitudinal axis A-A moves the engaging arms 85 to a position where they are free of the locking portion 86 and can be deflected by the force of the spring 25 to permit movement of the plunger 22 into the syringe, as shown in FIG. 4B. That is, rotation of the collar 80 moves the engaging arms 85 out of alignment with the locking portion 86 of the housing, allowing the engaging arms 85 to be deflected from the engaged position to release the plunger 22. The force of the spring 25 can cause the engaging arms 85 to deflect.

In the examples of FIGS. 3A to 4C, the collar 80 may be rotated by an actuator. For example, the device 20 may include a button that is pushed to rotate the collar 80, or a part of the housing 21 may be rotated to rotate the collar 80. Alternatively, a needle sleeve may be moved in a proximal direction when the injector device 20 is pushed against the skin, and the needle sleeve may engage the collar 80 during this proximal movement and cause the collar 80 to rotate and release the plunger 22. In these examples, the collar 80 may include an angled surface that can be pushed, for example by the needle sleeve, to cause the collar 80 to rotate.

Figure 5A:
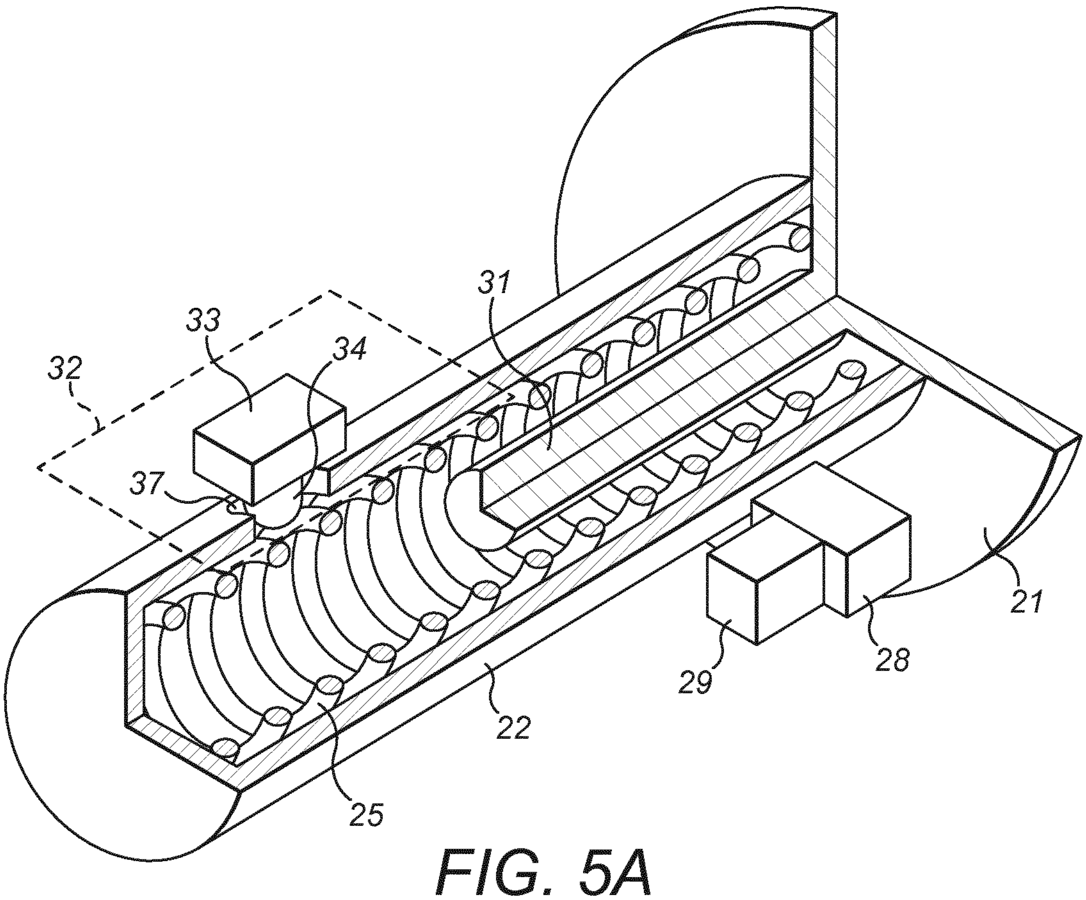
FIG. 5A is a cut-away perspective view of a part of the injector devices of FIG. 2A to 4B.
Figure 5B:
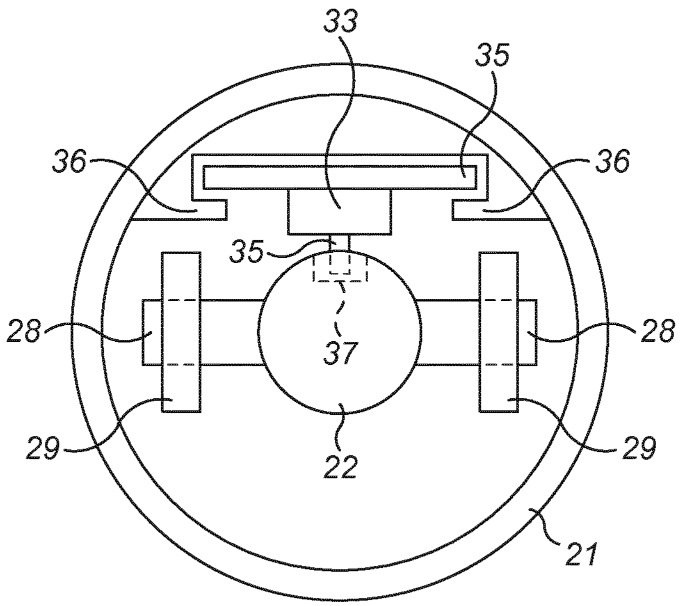
FIG. 5B is a cross-sectional end view of a part of the injector devices of FIG. 2A to 4B.

FIG. 5A and FIG. 5B show parts of the injector device 20 described with reference to FIGS. 2A to 4B, with the plunger 22, a part of the housing 21, and the spring 25 shown. As illustrated, this example of the injector device 20 also comprises an electronic system 32, shown here in dotted lines.

FIG. 5A and FIG. 5B show the plunger 22 and the locking tabs 28 that engage with parts 29 of the housing 21 arranged to latch the plunger 22 in the pre-dose position, with the spring 25 under compression. In this example, the latch can be released by rotating the plunger 22 relative to the housing 21 until the locking tabs 28 pass over the parts 29 of the housing, allowing the plunger 22 to be pushed into the syringe (not shown) by the spring 25.

In this example, the electronic system 32 has a switch 33. The switch 33 is mounted within the housing 21 and engages with the plunger 22. In particular, the switch 33 comprises an engaging member 34 that is urged towards the plunger 22 but can be deflected inwards to change the state of the switch 33.

In this example, the electronic system 32 also includes an electronic circuit board 35, on which the switch is mounted, as shown in FIG. 5B. The electronic circuit board 35 is mounted in the housing 21 and is held in place by mounting features 36 of the housing 21, as illustrated in FIG. 5B. In various examples, the mounting features 36 may be a slot, or snap-fit flaps, or fasteners, for example screws or clips.

In various examples, as described hereinafter, the electronic system 32 may optionally include a power source, for example a battery, a controller, and other electronic components, such as resistors, capacitors and the like. The controller may comprise a processor and/or a memory.

Also shown in FIG. 5A and FIG. 5B, the plunger 22 comprises a recess 37 that is arranged to be detected by the switch 33 as the plunger 22 is pushed into the syringe 23, as explained in more detail hereinafter.

Figure 6:
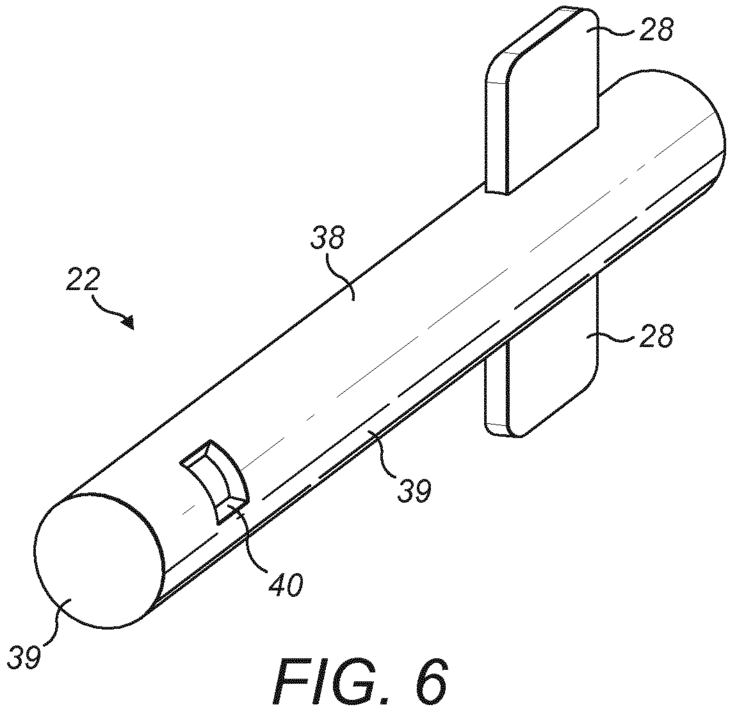
FIG. 6 is a perspective view of the plunger of the injector device of FIG. 2A to FIG. 3B.

FIG. 6 shows the plunger 22 of the injector device 20 described above. As shown, the plunger 22 has locking tabs 28 described with reference to FIGS. 2A, 2B, 3A, 3B, 4A, 4B, 5A and 5B, and an elongate cylindrical body 38. The elongate cylindrical body 38 is forced into the syringe (23, see FIG. 2B) by the spring (25, see FIG. 2B) during use. An end 39A of the elongate cylindrical body 38 is the piston, or the end 39A of the elongate cylindrical body 38 abuts a piston (26, see FIG. 2B) located within the syringe (23, see FIG. 2B). The elongate cylindrical body 38 has an outer surface 39 with which the engaging member (34, see FIG. 5A) of the switch (33, see FIG. 5A) engages.

As shown in FIG. 6, the outer surface 39 of the plunger 22 has a recess 40. The recess 40 is positioned such that it is aligned with the engaging member (34, see FIG. 5A) of the switch (33, see FIG. 5A) as the plunger 22 moves from the pre-dose position (see FIG. 2A) to the post-dose position (see FIG. 2B). Note that in this example the position of the recess 40 takes into account the rotation of the plunger 22 to release the locking tabs 28. In other examples the plunger 22 is not rotated, and so the position of the recess 40 may vary accordingly.

In some embodiments the injector device 20 includes a window through which the syringe (23, see FIG. 2A) is visible, so that the user can see the plunger 22 move into the syringe and dispense medicament. In this case, the recess 40 may be disposed such that, after rotation of the plunger 22, the recess 40 is not visible through the window.

Returning to FIG. 5A and FIG. 5B, the switch 33 has two positions—a non-deflected position where the engaging member 34 is aligned with the recess 40 on the plunger 22 (and therefore the switch 33 is detecting the recess 40) and a deflected position where the engaging member 34 is deflected by the outer surface 39 of the plunger 22 (and is therefore not detecting the recess 40).

Figure 7A:
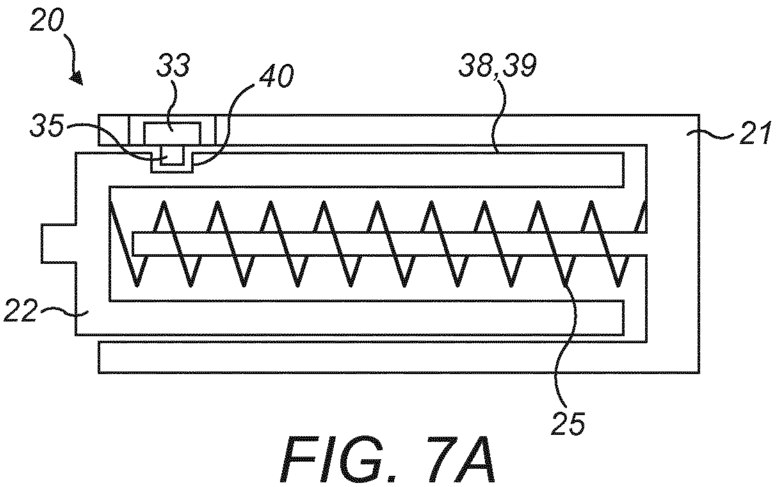
FIG. 7A is a schematic side view of an injector device having a spring to push a plunger into a syringe, the injector device is in a pre-dose position.
Figure 7B:
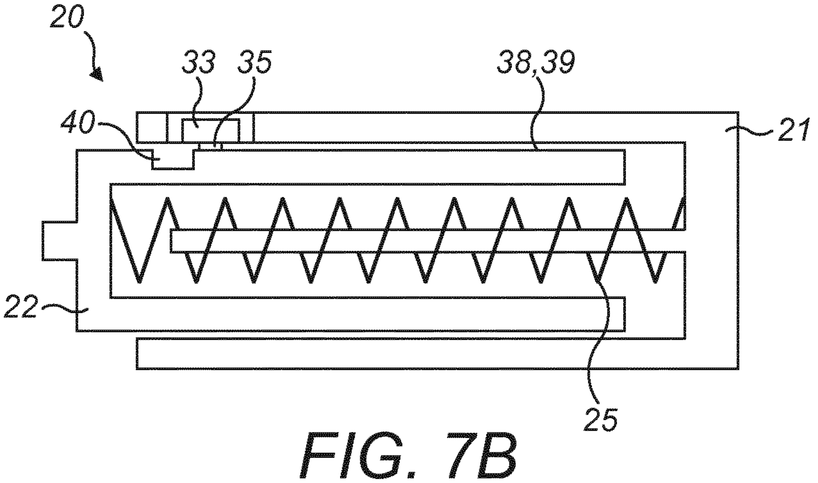
FIG. 7B is a schematic side view of the injector device of FIG. 7A, the injector device is at the start of an injection process.
Figure 7C:
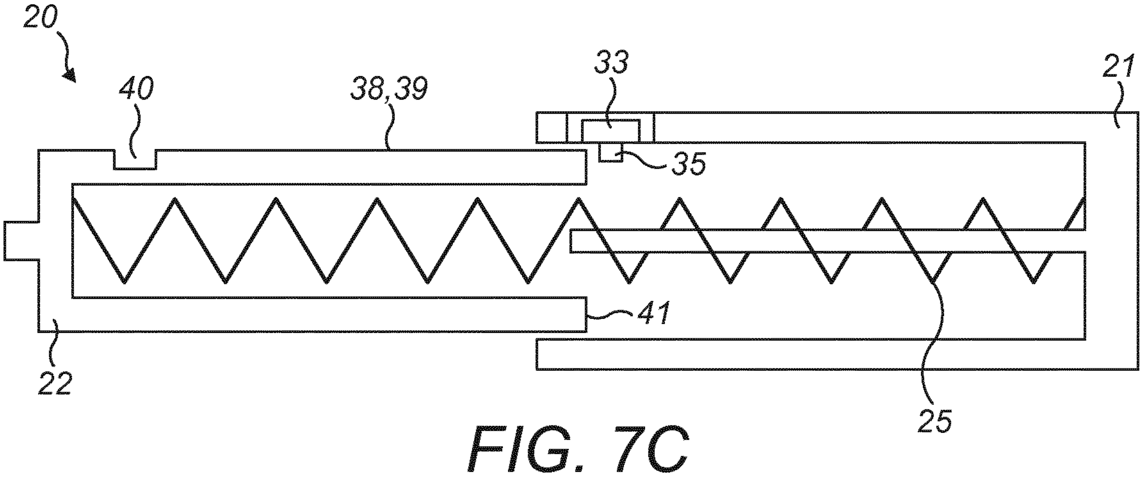
FIG. 7C is a schematic side view of the injector device of FIG. 7A and FIG. 7B, the injector device is in a post-dose position.

FIGS. 7A, 7B and 7C schematically illustrate the movement of the plunger 22 and the engagement of the switch 33. Each of FIGS. 7A, 7B and 7C shows the plunger 22, the recess 40, a part of the housing 21, the spring 25 and the switch 33. FIGS. 7A, 7B and 7C do not show the latch mechanism, for example the locking tabs 28 described previously.

FIG. 7A shows the injector device 20 in the pre-dose position, with the spring 25 under compression between the plunger 22 and the housing 21. In this position, the engaging member 35 of the switch 33 is aligned with the recess 40 on the plunger 22. The switch 33 is therefore in a first state, with the engaging member 35 in a non-deflected position.

In this pre-dose position, the electronic system is in an off-state. That is, the non-deflected arrangement of switch 33 position means that no power is provided to the electronic system. The electronic system is in a deep-sleep state, and no power is being used. The injector device 20 is manufactured and distributed in this state.

FIG. 7B shows the injector device 20 at the beginning of the injection process, as the latch has been disengaged and the spring 25 has begun to push the plunger 22 into the syringe (23, see FIG. 2B).

As shown, the recess 40 on the plunger 22 has moved and the engaging member 35 of the switch 33 is no longer aligned with the recess 40. The engaging member 35 of the switch 33 has been depressed by the outer surface 39 of the cylindrical body 38 of the plunger 22, changing the state of the switch 33. The switch 33 is therefore in a second state.

The electronic system is configured such that changing the state of the switch 33 activates the electronic system (turns on the power).

At this point, the electronic system may be configured to log the beginning of the injection process.

FIG. 7C shows the position of the plunger 22 after the injection process has been completed, that is, the post-dose position. In this position, the plunger 22 has reached its fully extended position and the medicament has been dispensed from the syringe 23. In this position, the end 41 of the plunger rod 22 has moved past the switch 33 so the engaging member 35 returns to its non-deflected position.

In one example, this change of state of the switch 33 can deactivate the electronic system. Alternatively the electronic system may include an electronic latch, for example a flip-flop circuit or a pair of cross-coupled NOR gates. The electronic latch can maintain power to the electronic system after the switch 33 has returned to the non-deflected state.

At this point, the electronic system may be configured to log the end of the injection process.

Figure 8A:
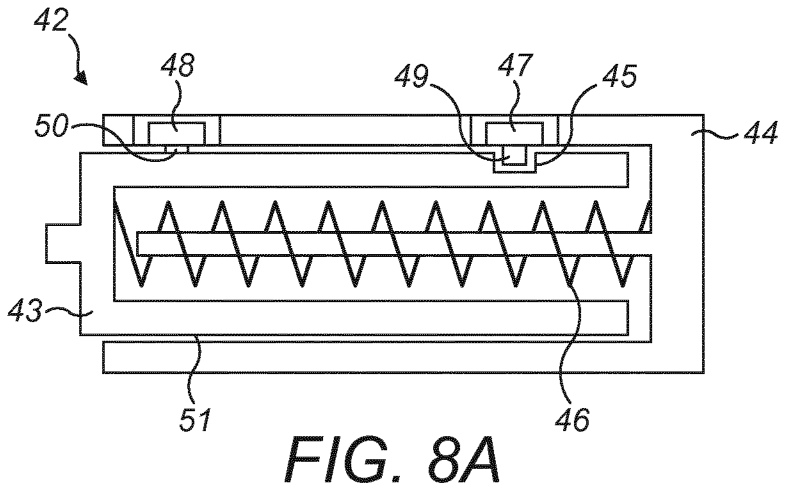
FIG. 8A is a schematic side view of an injector device having a spring to push a plunger into a syringe, the injector device is in a pre-dose position.
Figure 8B:
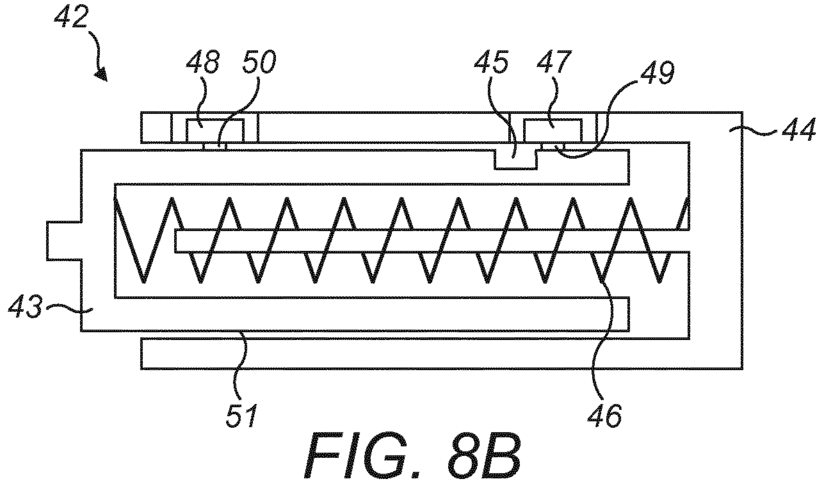
FIG. 8B is a schematic side view of the injector device of FIG. 8A, the injector device is at the start of an injection process.
Figure 8C:
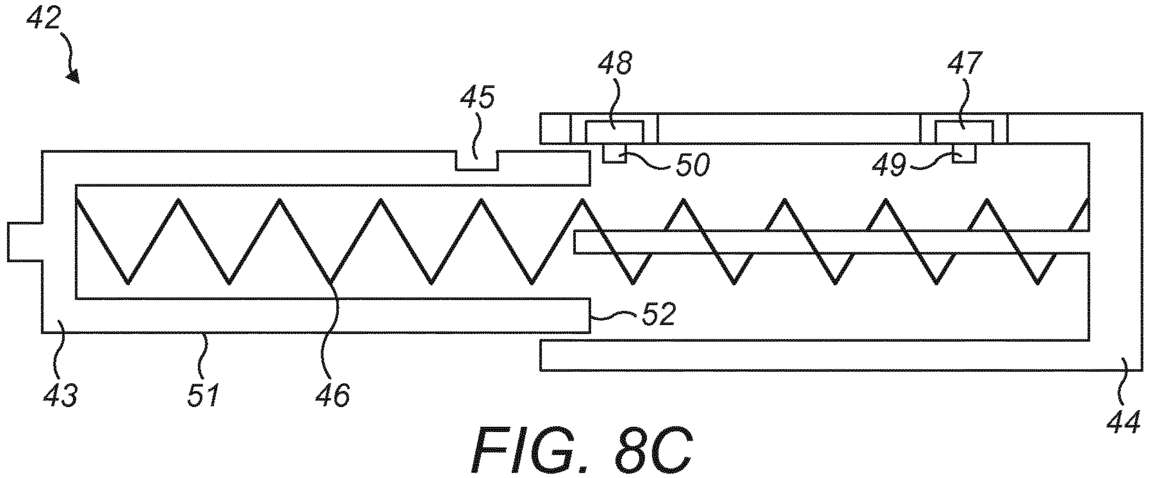
FIG. 8C is a schematic side view of the injector device of FIG. 8A and FIG. 8B, the injector device is in a post-dose position.

FIGS. 8A, 8B and 8C show an alternative example of an injector device 42, and in this example the injector device 42 has a plunger 43, recess 45, housing 44, and spring 46 that are similar to the examples of FIGS. 2A to 7C, described above. However, in this example, there is a first switch 47 and a second switch 48. FIGS. 8A, 8B and 8C schematically illustrate movement of the plunger 43 from the pre-dose position (FIG. 8A) to the post-dose position (FIG. 8C).

FIG. 8A shows the injector device 42 in the pre-dose position, with the spring 46 under compression between the plunger 43 and the housing 44. In this example, the recess 45 is in a different position to that described with reference to FIGS. 7A, 7B and 7C.

In this position, the engaging member 49 of the first switch 47 is aligned with the recess 45 in the plunger 43, such the that first switch 47 is in a non-deflected position. Meanwhile, the engaging member 50 of the second switch 48 is deflected by the outer surface 51 of the plunger 43, such that the second switch 48 in a deflected position.

In the state illustrated in FIG. 8A, the electronic system is in an off-state. That is, this particular arrangement of the positions of the first and second switches 47, 48 means that no power is provided to the electronic system. Therefore, the electronic system is in a deep-sleep state, and no power is being used. The injector device 42 is manufactured and distributed in this state.

FIG. 8B shows the injector device 42 at the beginning of the injection action, as the latch has been disengaged and the spring 46 has begun to push the plunger 43 into the syringe (not shown).

As shown, the recess 45 on the plunger 43 has moved and the engaging member 49 of the first switch 47 is no longer aligned with the recess 45—it is now deflected by the outer surface 51 of the plunger 43. The engaging member 50 of the second switch 48 is still deflected by the outer surface 51 of the plunger 43, as in FIG. 8A.

The electronic system is configured such that changing the state of the first switch 47 activates the electronic system (turns on the power).

At this point, the electronic system may be configured to log the start of the injection process.

FIG. 8C shows the position of the plunger 43 after the injection process has been completed, that is, the post-dose position when the plunger 43 has reached its fully extended position and the medicament has been completely dispensed from the syringe (not shown). In this position, the end 52 of the plunger 43 has moved past both of the first switch 47 and the second switch 48 so the engaging members 49, 50 of the first and second switches 47, 48 are in non-deflected positions.

At this point, the electronic system may be configured to log the end of the injection process.

Between the position of FIG. 8B (beginning of the injection process) and the position of FIG. 8C (the post-dose position) the recess 45 has moved past the second switch 48, which has therefore changed state from a deflected position, to a non-deflected position, and then back to a deflected position. The electronic system can be configured to ignore these particular changes of state of the second switch 48.

In alternative examples, the second switch 48 and/or recess 45 can be arranged such that the point at which the second switch 48 detects the recess 45 (i.e. when the second switch 48 moves to a non-deflected position) is at a significant position of the plunger 43, for example a minimum delivery position where a minimum dose of medicament has been delivered from the syringe (not shown).

Furthermore, between the position of FIG. 8B (beginning of the injection process) and the position of FIG. 8C (the post-dose position) the end 52 of the plunger 43 has moved past the first switch 47, which has therefore moved into a non-deflected position. The electronic system can be configured to ignore this change in state of the first switch 47.

In addition, the electronic system may be provided with an electronic latch (flip-flop) that maintains the power supply to the electronic system after the first switch 47 has returned to the non-deflected position as the end 52 of the plunger 43 passes the first switch 47.

In alternative examples, the first switch 47 and/or the recess 45 can be arranged such that the point at which the first switch detects 47 the recess (i.e. when the first switch 47 moves to a non-deflected position) is at a significant position of the plunger 43, for example a minimum delivery position where a minimum dose of medicament has been delivered from the syringe (not shown).

In other examples of the embodiments illustrated with reference to FIGS. 2A to 8C, the switch(es) 33, 47, 48 may interact with another structural element of the plunger 22, 43, other than a recess 40, 45. For example, the plunger 22, 43 may comprise a recess, protrusion, shoulder or other structural element that engages with the switch(es) 33, 47, 48. In some examples, the plunger 22, 43 dose not comprise any particular structural element, and the switch 33, 47, 48 detects the end 41, 52 of the plunger 22, 43.

As mentioned previously, the electronic system 32 may optionally include a power source, for example a battery, a controller, and other electronic components, such as resistors, capacitors and the like. The controller may comprise a processor and/or a memory.

As described above, by monitoring the positions of the switch(es) 33, 47, 48 it is possible to determine if the plunger 22, 43 is the pre-dose state (illustrated in FIG. 7A and FIG. 8A), if the plunger 22, 43 is at the beginning of the injection process (illustrated in FIG. 7B and FIG. 8B), and if the plunger 22, 43 is in the post-dose state (illustrated in FIG. 7C and FIG. 8C). The controller of the electronic system monitors the states of the switches 33, 47, 48. The controller may be adapted to log each of these positions, for example in the memory.

The switch(es) 33, 47, 48 and recesses 40, 45 can be arranged such that the switch(es) 33, 47, 48 detect the plunger 22, 43 at any location along the movement of the plunger 22, 43 from the pre-dose position to the post-dose position.

Additionally or alternatively, the controller may be adapted to provide a signal to a display. For example, the injector device 20, 42 may comprise one or more LED indicators or LCD displays that are adapted to display indications that the plunger 22, 43 is in a certain position.

In one example, the injector device 20, 42 comprises an LED indicator and the controller is configured to provide signals to the LED indicator such that the LED indicator is: switched off in the pre-dose position (illustrated in FIG. 7A and FIG. 8A); switched to red at the beginning of the injection process (illustrated in FIG. 7B and FIG. 8B); and switched to green in the post-dose position (illustrated in FIG. 7C and FIG. 8C).

In another example, the injector device 20, 42 may comprise more than one LED indicator to provide such indication to the user. For example a first LED that is switched on at the beginning of the injection process (illustrated in FIG. 7B and FIG. 8B), and a second LED that switched on in the post-dose position (illustrated in FIG. 7C and FIG. 8C).

In another example, the injector device 20, 42 may comprise an LCD display or other similar display, and the controller may be configured to provide signals to the LCD display such that the LCD display displays information about the position of the plunger 22, 43. For example, the LCD display may display text or symbols that indicate that the plunger 22, 43 is: in a pre-dose position (illustrated in FIG. 7A and FIG. 8A); at the beginning of the injection process (illustrated in FIG. 7B and FIG. 8B); and/or in the post-dose position (illustrated in FIG. 7C and FIG. 8C).

In this way, the switches 33, 47, 48 and controller inform the user about the status of the injection process. In particular, the user can be informed that the injection process has begun and can be informed that the injection process is complete. This is information is based on the position of the plunger 22, 43, so is a reliably accurate indication of the injection process.

In further examples, the electronic system includes a communication device. The communication device may be configured to receive information from the controller and to communicate with a further device.

In one example, the communication device comprises a transmitter, for example a radio transmitter. In another example, the communication device comprises a BLUETOOTH® device. In another example, the communication device comprises a near-field communication (NFC) chip or device.

The further device may for example be an auxiliary device for communicating with the injector device. In this example, the auxiliary device may connect with more than one injector device. In other examples, the further device may be a smartphone or other handheld electronic device. The auxiliary device or the handheld electronic device may have software, for example an application (app), for connecting with, and receiving information from, the injector device 20, 42.

In these examples, the further device may comprise a memory which stores information relating to use of the injection device 20, 42. For example, the further device may log that one injection process was completed on a particular date at a particular time, or it may log that one injection process was started but not completed. In this way, users and/or medical professionals and/or other interested parties can review use of the injector device(s), for example to ensure correct use. Additionally, the further device may be configured to generate a warning of incomplete or inadequate use of the injector device 20, 42.

Additionally or alternatively, the further device may be configured to send information relating to the use of the injection device 20, 42 to a further device or a server, such that multiple parties can access the information. Statistical analysis may be conducted on this information, possibly over a large group-set, to analyse patterns of use of the injector devices 20, 42.

The communication device may include an antenna. The antenna may be located within the housing 21, 44, or it may be embedded within the housing 21, 44, or it may be disposed on an outer surface of the housing 21, 44. In another example, the antenna is embedded within a panel that comprises a part of the housing 21, 44. This is advantageous for low power transmitters or NFC, as there will be less material between the antenna and the exterior of the injector device 20, 42, allowing for better communication with the further device. The antenna may be connected to an external surface of the housing 21, 44 and the antenna may be connected with internal electronics, for example the controller. The connection may be via connection pins or other conductive connection that extends from the antenna. In one preferred example, the antenna is incorporated into an adhesive label that is applied to the exterior of the housing 21, 44 during assembly. The adhesive label may include connection pins that provide an electrical connection to electronic components within the housing 21, 44.

Figure 9A:
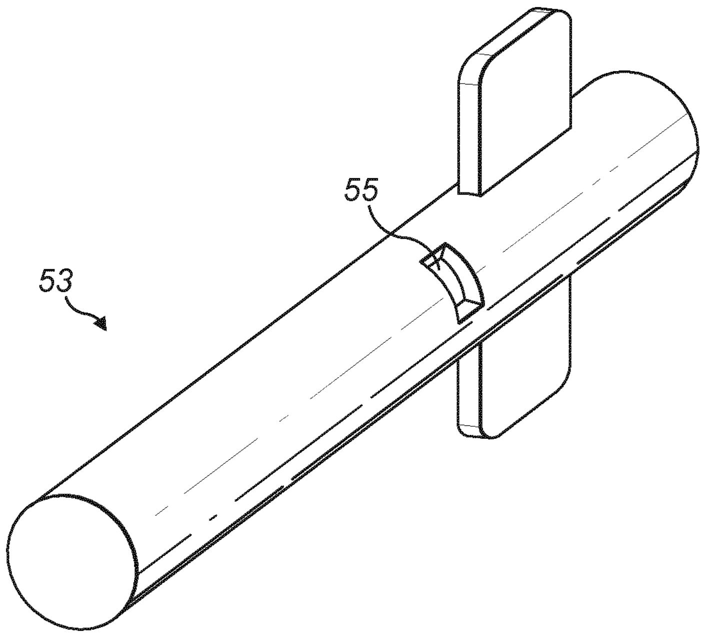
FIG. 9A is a perspective view of an alternative plunger for the injector device of any of FIG. 2A to FIG. 8C.
Figure 9B:
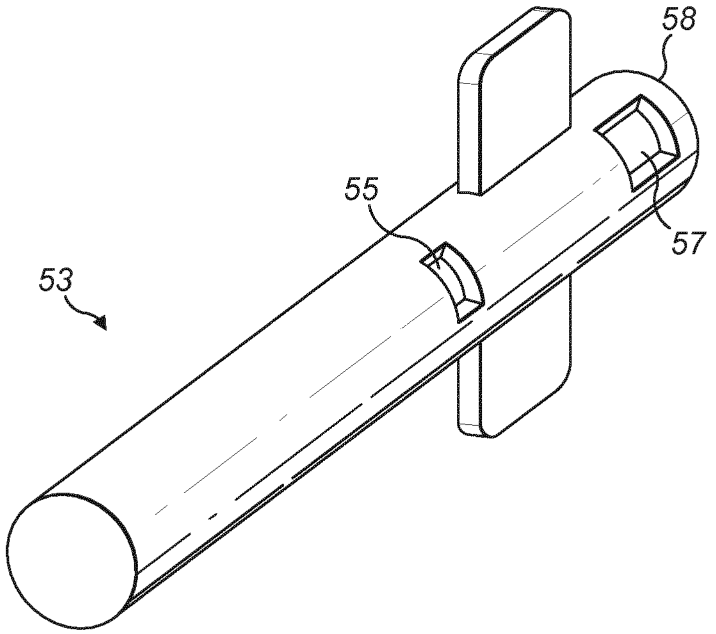
FIG. 9B is a perspective view of an alternative plunger for the injector device of any of FIG. 2A to FIG. 8C.

FIG. 9A and FIG. 9B show alternative examples of the plunger 53, 54 that may replace the plunger 22, 43 in the examples of FIGS. 7A to 7C or in the examples of FIGS. 8A to 8C.

In the example illustrated in FIG. 9A, the plunger 53 is longer than the example plunger 22 of FIG. 6. Such a longer plunger 53 may be used if the dose of the syringe (23, see FIG. 2B) is less, and so the piston (26, see FIG. 2B) of the plunger 53 has a starting position further towards the needle (24, see FIG. 2B) than in the example shown in FIG. 4. The longer plunger 53 may have a recess 55 arranged as per the recess 40 of the example of FIGS. 7A to 7C or as per the recess 45 of the example of FIG. 8A to 8C.

In the example illustrated in FIG. 9B, the plunger 54 is provided a first recess 56 and a second recess 57, each being aligned with the engaging member(s) 35, 49, 50 of the switch(es) 33, 47, 48 described with reference to FIGS. 7A to 8C. The second recess 57 is provided proximate to the end 58 of the plunger 54. The second recess 57 is therefore arranged to replace the function of the end 58 of the plunger 54 in the example of FIGS. 7A to 7C and FIGS. 8A to 8C, so that the switch(es) 33, 47, 48 detects the second recess 57 at the end of the injection process and not the end 58 of the plunger 54.

FIG. 9C shows another plunger 53A that may replace the plunger 22, 43 in the examples of FIGS. 7A to 7C or in the examples of FIGS. 8A to 8C. The plunger 53A is the same as the plunger 53 of FIG. 9A except that the recess 55 is omitted and is replaced by a structural element in the form of a protrusion 55A that engages with the switch(es) 33, 47, 48.

In some embodiments the injector device 20, 42 includes a window through which the syringe (23, see FIG. 2A) is visible, so that the user can see the plunger 53, 54 move into the syringe and dispense medicament. In these embodiments, the recesses 55, 56, 57 are located such that they are not visible through the window. In particular, the recesses 55, 56, 57 are disposed on a part of the plunger 53, 54 that does not extend into the syringe, so is not visible through the window. Alternatively, the recesses 55, 56, 57 may be disposed such that, after rotation of the plunger 53, 54, the recesses 55, 56, 57 are not visible through the window.

In other examples, the electronic system of the injector device 20, 42 has a sensor that detects an operating parameter of the injector device 20, 42. For example, the electronic system may include a temperature sensor to detect a temperature of the injector device 20, 42 and/or the medicament in the syringe 23. This information may also be communicated to a further device by the communication device. This may be useful, for example, to check that the medicament is at an appropriate temperature before the injection process is started.

In some examples, as described with reference to FIGS. 1A and 1B, the injector device 20, 42 may include a needle sleeve 19 that is moved within the housing 21, 44 during use of the device 20, 42. In one example, movement of the needle sleeve 19 may release the latch that holds the plunger 22, 43 in the pre-dose position. For example, movement of the needle sleeve 19 may cause rotation of the plunger 22, 43, which may release a latch and allow the plunger 22, 43 to move into the syringe 23. In another example, movement of the needle sleeve 19 may directly cause the plunger 22, 43 to be pushed into the syringe 23.

In these examples, the electronic system of the injector device 20, 42 may have a sensor that detects movement of the needle sleeve 19. For example, the electronic system may include a sensor that detects when the needle sleeve 19 has moved into a position in which the latch is moved and the spring 25, 46 is free to push to plunger 22, 43 into the syringe 23. In this way, the electronic system is able to determine that the device is being used.

Figure 10A:
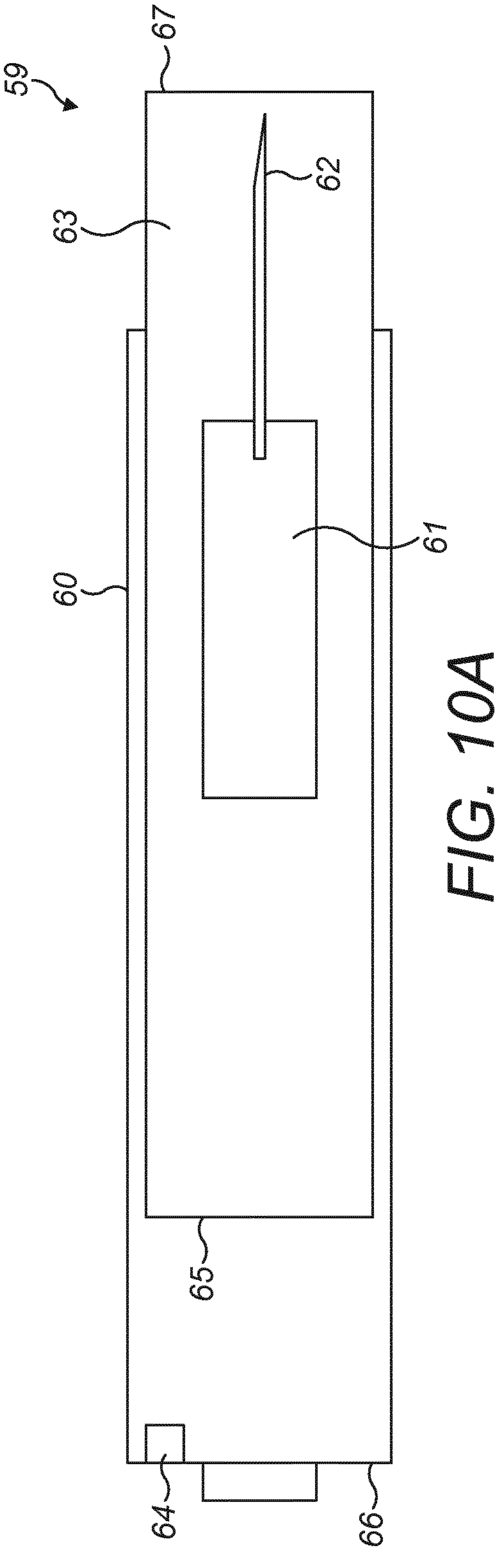
FIG. 10A is a schematic side view of an injector device having a needle sleeve that is movable within the housing, the injector device is in a pre-dose position.
Figure 10B:
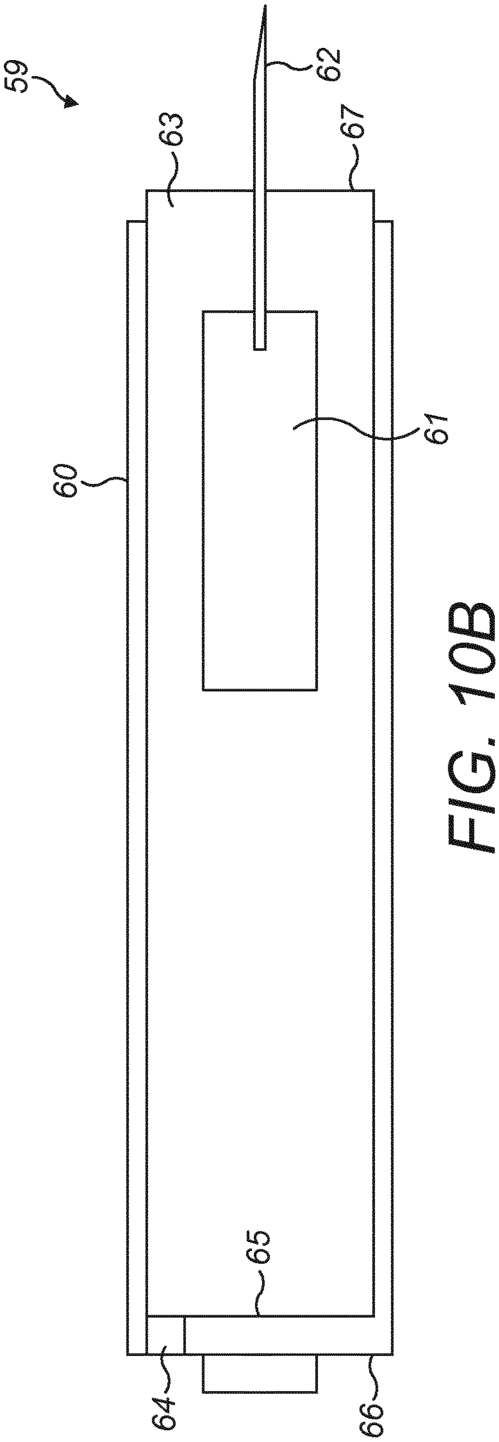
FIG. 10B is a schematic side view of the injector device of FIG. 10A, the injector device is in a post-dose position.

FIGS. 10A and 10B show a schematic diagram of another example of an injector device 59 having a housing 60, a syringe 61, a needle 62, and an actuator 63. In this example, the actuator 63 is a needle sleeve. The injector device 59 has a sensor 64 that may be provided in addition to, or instead of, the sensors (e.g. switches 33, 47, 48) previously described.

FIG. 10A shows a pre-dose position, where the needle sleeve 63 is in an extended position. In this position the needle sleeve 63 surrounds and protects the needle 62. In this position, a proximal end 65 of the needle sleeve 63 is spaced from a proximal end 66 of the housing 60.

When the injector device 59 is used, the distal end 67 of the needle sleeve 63 is pushed against the skin of the user and the needle sleeve 63 is thereby pushed into the housing 60. This causes the needle 62 to be revealed and thereby pierce the skin. In addition, as the needle sleeve 63 slides into the housing 60 the proximal end 65 of the needle sleeve 63 reaches the proximal end 66 of the housing 60, as shown in FIG. 8B.

A sensor 64, for example a switch, proximity sensor or optical sensor, is provided at either the proximal end 66 of the housing 60 (as shown) or at the proximal end 65 of the needle sleeve 63. Therefore, the sensor 64 can detect when the needle sleeve 63 has been pushed into the housing 60, and therefore that injection process has begun.

In addition, movement of the needle sleeve 63 into the housing may release a latch, as previously explained, which may trigger a spring-loaded injection system. In this example, the sensor 64 can detect that the needle sleeve 63 has reached the point at which the latch is released.

In a further example, a biasing member (not shown) urges the needle sleeve 63 towards the position shown in FIG. 10A, i.e. out of the housing 60. In this way, after the injector device 59 has been removed from the skin the needle sleeve 63 will return to the position of FIG. 10A. This can be detected by the sensor 64 and so the sensor 64 can detect the end of the injection process.

As with the examples of FIGS. 7A to 7C and FIGS. 8A to 8C, the electronic system may include a controller and/or a communication device to process, store and or transmit information provided by the sensor 64.

In other examples, the injector device comprises an alternative actuator, for example a button or lever, that starts the injection process. In these examples, a sensor may be arranged to detect a position of the actuator. The actuator may directly push the plunger into the syringe, or the actuator may release or unlatch a pre-loaded mechanism, for example to previously described spring mechanism. Preferably, the actuator directly causes the injection process to occur, e.g. releases a spring-loaded mechanism, so that the sensor provides reliable information relating to the injection process.

Figure 11:
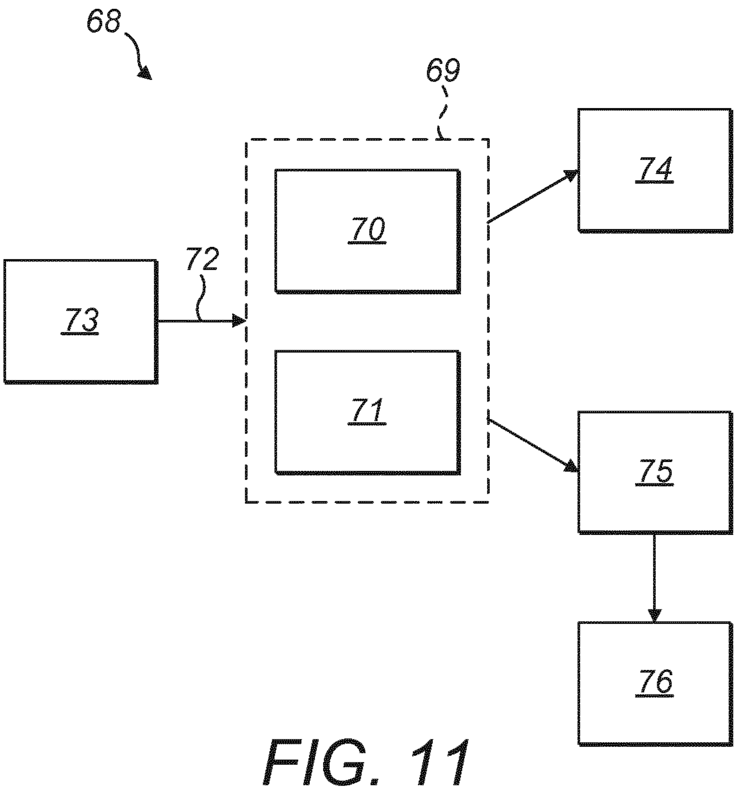
FIG. 11 is a block diagram illustrating an electronic system of the injector device of any of FIGS. 2A to 8B.

FIG. 11 shows a process diagram for the electronic system 68 for the injector devices 10, 20, 42, 59 previously described. As shown, the electronic system 68 comprises a controller 69. The controller optionally includes a processer 70 and a memory 71. The controller 69 is configured to receive information 72 from a sensor 73, for example switch(es) 33, 47, 48 or sensor 64.

The sensor 73 is adapted to detect one or more parameter associated with operation of the injector device 10, 20, 42, 59. As explained in previous examples, that parameter may be the position of a plunger 22, 43 within the injector device 20, 42, or the parameter may be the position of a needle sleeve 63. Alternatively or additionally, a sensor may detect a temperature of the device or medicament.

The controller 69 is configured to process and/or store information received from the sensor 73. The injector device 10, 20, 42, 59 optionally also includes a feedback device that the controller 69 communicates with to provide feedback to the user. For example, the controller 69 may be configured to control a display 74, for example one or more LEDs or an LCD display, to provide visual feedback to the user. Alternatively, the controller 69 may be configured to communicate the information using a communication device 75. As described previously, the communication device 75 may communicate with a further device 76 that may provide feedback to the user.

In one example, the communication device 75 comprises a transmitter, for example a radio transmitter. In another example, the communication device 75 comprises a BLUETOOTH® device. In another example, the communication device 75 comprises a near-field communication (NFC) chip or device. The communication device 75 may comprise an antenna 75A, as previously described.

The further device 76 may for example be an auxiliary device for communicating with the injector device 20, 42. In this example, the auxiliary device may connect with more than one injector device 20, 42. In other examples, the further device 76 may be a smartphone or other handheld electronic device. The auxiliary device or the handheld electronic device may have software, for example an application (app), for connecting with, and receiving information from, the injector device 20, 42.

In these examples, the further device 76 may comprise a memory which stores information relating to use of the injection device 20, 42. For example, the further device 76 may log that one injection process was completed on a particular date at a particular time, or it may log that one injection process was started but not completed. In this way, users and/or medical professionals and/or other interested parties can review use of the injector device(s), for example to ensure correct use. Additionally, the further device may be configured to generate a warning of incomplete or inadequate use of the injector device 20, 42.

Additionally or alternatively, the further device 76 may be configured to send information relating to the use of the injection device 20, 42 to a further device or a server, such that multiple parties can access the information. For example, the further device 76 may upload information to a server via a cloud connection. Statistical analysis may be conducted on this information, possibly over a large groupset, to analyse patterns of use of the injector devices 20, 42 for individual users or groups or users.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term “antibody”, as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms “fragment” or “antibody fragment” refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms “Complementarity-determining region” or “CDR” refer to short polypeptide sequences within the variable region of both heavy and light chain polypeptides that are primarily responsible for mediating specific antigen recognition. The term “framework region” refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. An injector device comprising:

a housing;

a container;

a plunger that is movable into the container to dispense medicament during operation of the injector device;

an electronic system comprising a switch mounted within the housing and arranged to interact with a structural element of the plunger to detect movement of the plunger during the operation of the injector device, wherein the switch comprises a mechanical switch having an engaging member that is biased into contact with the plunger such that the engaging member engages the structural element of the plunger when the structural element passes the engaging member, wherein the switch has a first state, in which no power is provided to the electronic system and the electronic system is in an off-state, and a second state, and wherein the engaging member is deflectable from a first position in which the switch is in the first state to a second position in which the switch is in the second state to turn on the power to the electronic system when the plunger is moved from a pre-dose position, wherein, in one of the first state or the second state, the engaging member is engaged with an outer surface of a body of the plunger, and in another of the first state or the second state, the engaging member is engaged with the structural element, and wherein the structural element of the plunger is a recess or a protrusion;

a biasing member arranged to push the plunger into the container during the operation of the injector device, wherein the biasing member is configured to exert an axial force on the plunger to push the plunger into the container; and a latch arranged to hold the plunger in an initial position where the biasing member is under compression prior to the operation of the injector device, wherein the plunger is configured to be rotated to disengage the latch from holding the plunger such that the biasing member is able to push the plunger into the container, and wherein the plunger is configured to slide into the container under the axial force of the biasing member once the latch has been disengaged.

2. The injector device of claim 1, wherein the structural element of the plunger is an end of the plunger.

3. The injector device of claim 1, wherein the switch is arranged to detect the recess or the protrusion of the plunger; and wherein the injector device further comprises a second switch arranged to detect an end of the plunger as the plunger moves into the container.

4. The injector device of claim 1, wherein the switch is arranged to detect the structural element of the plunger when the plunger is rotated to disengage the latch.

5. The injector device of claim 1, wherein the latch comprises a collar that surrounds a part of the plunger and engages the plunger to hold the plunger in the initial position.

6. The injector device of claim 5, wherein the plunger is arranged to be rotated relative to the collar to release the plunger for movement into the container.

7. The injector device of claim 1, further comprising a communication device configured to receive a signal output by the switch.

8. The injector device of claim 7, wherein the communication device comprises an antenna.

9. The injector device of claim 1, further comprising a processing unit configured to receive a signal output by the switch.

10. The injector device of claim 9, wherein movement of the switch between the first state and the second state causes at least one of: the processing unit to be powered on and/or the processing unit to be powered off.

11. The injector device of claim 1, further comprising a feedback device configured to provide a user with information relating to the movement of the plunger during the operation of the injector device.

12. The injector device of claim 1, wherein the container further comprises a reservoir that holds the medicament, wherein the medicament is a liquid.

13. The injector device of claim 1, wherein a signal output by the switch is dependent on whether the engaging member is in the first position or has been deflected to the second position.

14. The injector device of claim 1, wherein the structural element is fixed relative to the plunger such that the structural element does not move relative to the plunger.

15. The injector device of claim 1, wherein the switch is arranged to detect a start of the movement of the plunger and/or an end of the movement of the plunger.

16. The injector device of claim 1, further comprising a needle sleeve slidably mounted in the injector device and arranged such that during use the needle sleeve slides into engagement with the plunger to cause the plunger to rotate and disengage the latch.

17. A method of manufacturing an injector device, the method comprising:

arranging a container and a plunger in a housing such that the plunger is moveable into the container to dispense medicament during operation of the injector device under action of a biasing member pushing the plunger into the container upon the plunger being rotated to disengage a latch from holding the plunger, wherein the biasing member is configured to exert an axial force on the plunger to push the plunger into the container, and wherein the plunger is configured to slide into the container under the axial force of the biasing member once the latch has been disengaged; and providing an electronic system comprising a switch mounted within the housing and arranged to interact with a structural element of the plunger to detect movement of the plunger during the operation of the injector device, wherein the switch comprises a mechanical switch having an engaging member that is biased into contact with the plunger such that the engaging member engages the structural element of the plunger when the structural element passes the engaging member, wherein the structural element of the plunger is a recess or a protrusion, wherein the switch has a first state, in which no power is provided to the electronic system and the electronic system is in an off-state, and a second state, and wherein the engaging member is deflectable from a first position in which the switch is in the first state to a second position in which the switch is in the second state to turn on the power to the electronic system when the plunger is moved from a pre-dose position, wherein, in one of the first state or the second state, the engaging member is engaged with an outer surface of a body of the plunger, and in another of the first state or the second state the engaging member is engaged with the structural element.

* * * * *